US012755463B2

(12) United States Patent
Eichner et al.

(10) Patent No.: US 12,755,463 B2
(45) Date of Patent: Oct. 6, 2026

(54) OPTIMIZATION OF EXTRAORAL PANORAMIC IMAGES THROUGH MODEL-BASED PRIOR KNOWLEDGE OF THE PATIENT'S JAW ARCH FORM

(71) Applicants: DENTSPLY SIRONA INC., York, PA (US); SIRONA DENTAL SYSTEMS GMBH, Bensheim (DE)

(72) Inventors: Stefan Eichner, Heidelberg (DE); Michael Elvers, Darmstadt (DE)

(73) Assignee: Dentsply Sirona Inc., York, PA (US)

( * ) Notice: Subject to any disclaimer, the term of this patent is extended or adjusted under 35 U.S.C. 154(b) by 296 days.

(21) Appl. No.: 18/681,263

(22) PCT Filed: Jul. 26, 2022

(86) PCT No.: PCT/EP2022/070891
§ 371 (c)(1),
(2) Date: Feb. 5, 2024

(87) PCT Pub. No.: WO2023/011977
PCT Pub. Date: Feb. 9, 2023

(65) Prior Publication Data
US 2024/0338865 A1 Oct. 10, 2024

(30) Foreign Application Priority Data
Aug. 6, 2021 (EP) .................................... 21190056

(51) Int. Cl.
*G06T 11/00* (2026.01)
*A61B 6/51* (2024.01)
(Continued)

(52) U.S. Cl.
CPC ................ *G06T 12/10* (2026.01); *A61B 6/51* (2024.01); *G06T 15/00* (2013.01)

(58) Field of Classification Search
CPC ........... G06T 12/10; G06T 15/00; A61B 6/51; A61B 6/4021; A61B 6/545
See application file for complete search history.

(56) References Cited

U.S. PATENT DOCUMENTS

2013/0094748 A1* 4/2013 Shi .......................... A61B 6/51
378/38
2017/0007191 A1* 1/2017 Zoccatelli ............. A61B 6/501
(Continued)

FOREIGN PATENT DOCUMENTS

EP 2465436 A1 6/2012
EP 2614773 A1 7/2013
(Continued)

OTHER PUBLICATIONS

International Search Report; PCT/EP2022/070891; Oct. 27, 2022 (completed); Nov. 8, 2022 (mailed).
(Continued)

*Primary Examiner* — Oneal R Mistry
*Assistant Examiner* — Jongbong Nah
(74) *Attorney, Agent, or Firm* — SCHWEGMAN LUNDBERG & WOESSNER, P.A.

(57) ABSTRACT

The disclosure relates to a method including: (S1) Determining the jaw arch form as a model-based prior knowledge about the anatomy of a patient based on one or more previous panoramic images or 3D images or one or more optical 3D scans of the patient; (S2) Determining a patient-specific x-ray device imaging trajectory for the panoramic image of the patient; (S3) Performing the imaging on the basis of the determined patient-specific x-ray device imaging trajectory to acquire imaging data; (S4) Adjusting reconstruction parameters according to the determined patient-specific x-ray device imaging trajectory; (S5) Determining the patient-specific focal curve for the panoramic image of the patient to be produced by using the model-based prior
(Continued)

knowledge; (S6) Reconstructing the panoramic image using the acquired imaging data, the adjusted reconstruction parameters including the determined patient-specific focal curve, and a layer to be imaged which overlaps with the determined jaw arch

5 Claims, 2 Drawing Sheets

(51) Int. Cl.
*G06T 12/10* (2026.01)
*G06T 15/00* (2011.01)

(56) References Cited

U.S. PATENT DOCUMENTS

| | | | | |
|---|---|---|---|---|
| 2019/0026889 | A1* | 1/2019 | Salah | A61C 7/002 |
| 2020/0234404 | A1* | 7/2020 | Wiese | A61B 6/512 |
| 2021/0196434 | A1* | 7/2021 | Cramer | G06T 7/0012 |
| 2021/0407159 | A1* | 12/2021 | Eichner | A61B 6/51 |
| 2024/0016446 | A1* | 1/2024 | Kim | G06T 7/0012 |
| 2024/0169607 | A1* | 5/2024 | Han | G01N 23/046 |

FOREIGN PATENT DOCUMENTS

| | | | |
|---|---|---|---|
| EP | 3711672 | A1 | 9/2020 |
| EP | 4129191 | | 2/2023 |
| EP | 4380459 | | 6/2024 |
| JP | 2024529065 | | 8/2024 |
| WO | 2019002631 | | 1/2019 |
| WO | 2019063797 | | 4/2019 |
| WO | 2019063797 | A1 | 4/2019 |
| WO | 2023011977 | | 2/2023 |

OTHER PUBLICATIONS

Written Opinion of the International Searching Authority; PCT/EP2022/070891; Oct. 27, 2022 (completed); Nov. 8, 2022 (mailed).

"European Application Serial No. 21190056.8, Communication Pursuant to Article 94(3) EPC mailed Oct. 28, 2024", w Machine English Translation, 13 pgs.

"International Application Serial No. PCT EP2022 070891, International Preliminary Report on Patentability mailed Feb. 15, 2024", 7 pgs.

"European Application Serial No. 21190056.8, Extended European Search Report mailed Feb. 7, 2022", w English Search Report, 7 pgs.

"European Application Serial No. 21190056.8, Response filed Aug. 8, 2023 to Extended European Search Report mailed Feb. 7, 2022", w English Claims, 23 pgs.

"European Application Serial No. 22755176.9, Response to Communication pursuant to Rules 161(1) and 162 EPC filed Sep. 3, 2024", 21 pgs.

"European Application Serial No. 21190056.8, Response Filed Apr. 28, 2025 to Communication Pursuant to Article 94(3) EPC mailed Oct. 28, 2024", 14 pgs.

"European Application Serial No. 22755176.9, Communication pursuant to Article 94(3) EPC mailed Jun. 4, 2025", 5 pgs.

* cited by examiner

OPTIMIZATION OF EXTRAORAL PANORAMIC IMAGES THROUGH MODEL-BASED PRIOR KNOWLEDGE OF THE PATIENT'S JAW ARCH FORM

CROSS-REFERENCE TO RELATED APPLICATIONS

This is a National Phase application of International Application No. PCT/EP2022/070891, filed Jul. 26, 2022, which claims the benefit of and priority to European Application Ser. No. 21190056.8 filed on Aug. 6, 2021, which are herein incorporated by reference for all purposes.

The entire content of the priority application EP21190056.8 is hereby incorporated by reference to this international application under the provisions of the PCT.

TECHNICAL FIELD OF THE INVENTION

The present invention relates to methods for producing digital panoramic images using extraoral X-ray devices.

BACKGROUND OF THE INVENTION

When producing a panoramic image, a default imaging trajectory of an extraoral X-ray device maps an empirically found default focal curve in the patient's jaw. In the event of a deviation from this reference, whether due to incorrect positioning of the patient or a jaw arch form that deviates from the default focal curve, there occurs a deterioration in the panoramic image quality.

Usually, a downstream autofocus procedure is used to find the optimal sharpness locally within the panoramic image. Strong anatomical anomalies and/or unfavorable x-ray beam angles cannot be corrected with this procedure. These procedures are always downstream software solutions, so that a more elaborate reconstruction becomes necessary, which can, however, only use the generated data based on the default imaging trajectory.

SUMMARY OF THE INVENTION

Currently, the inventors are not aware of any prior art in which the default imaging trajectory and the default focal curve to be reconstructed can be accurately matched to the patient's jaw arch using prior knowledge of the patient's anatomy.

An objective of the present invention is to provide a method for producing digital panoramic images using extraoral X-ray devices that can overcome the above-mentioned disadvantages of the prior art.

The present invention provides a computer implemented method for producing digital panoramic images of a patient using an extraoral X-ray device. The method comprises the following steps of: Determining the jaw arch form as a model-based prior knowledge about the anatomy of a patient based on one or more previous panoramic images or 3D images or optical 3D scans of the patient; Determining a patient-specific x-ray device imaging trajectory for the panoramic image of the patient to be produced by using the said model-based prior knowledge so that the determined jaw arch from, in particular the position of the teeth thereof can be optimally exposed and imaged; Performing the imaging on the basis of the determined patient-specific x-ray device imaging trajectory in order to acquire imaging data; Adjusting or newly setting reconstruction parameters of the x-ray device according to the determined patient-specific x-ray device imaging trajectory; Determining the patient-specific focal curve for the panoramic image of the patient to be produced by using the said model-based prior knowledge so that the determined jaw arch form in particular the position of the teeth therein can be optimally reconstructed; Reconstructing the panoramic image using the acquired imaging data, the adjusted or newly set reconstruction parameters including the determined patient-specific focal curve, and a layer to be imaged which overlaps with the determined jaw arch form, wherein the patient-specific focal curve lies within said layer to be imaged; and Displaying the reconstructed panoramic image.

An advantageous effect of the present invention is that, in sum, it creates added diagnostic value for the physician due to the improved panoramic image quality. Repeat exposures and additional scout shots are avoided by virtue of using previous patient specific data. Thereby the dose can be reduced or the image quality improved.

A further advantageous effect of the present invention is that the jaw arch form or the jaw arch geometry can be derived for the patient on the basis of a previous panoramic image, a previous 3D volume image or a previous surface scan in order to determine the appropriate patient specific imaging trajectory and the appropriate patient specific focal curve so that the reconstruction, and thus the panoramic image can be entirely patient-specific. It is also possible to use a patient-specific partial imaging trajectory and a patient-specific partial focal curve to create patient-specific partial sections of a panoramic image.

In an advantageous embodiment, one or more neural networks are used. The jaw arch form can be determined using neural networks. The neural networks are trained by data pairs comprising 3D volumes and the jaw arch forms respectively marked therein, or comprising the optical 3D scans and the jaw arch forms respectively marked therein. For this purpose, the jaw arch shape may have been marked manually or automatically by image processing while considering anatomical dental features of the patient.

In an advantageous embodiment in the reconstruction of the panoramic image, the overlap of the jaw arch and the layer to be imaged is maximal, wherein the patient-specific focal curve lies within the imaging layer and best possible maps the upper and lower jaw arch.

The invention also provides a computerized extraoral x-ray system to perform the method. The extraoral X-ray system can acquire the imaging data and provide the reconstructed panoramic image, wherein the computational steps can be performed on the same extraoral X-ray system or on a separate remote computer thereof which may be local or in the cloud.

BRIEF DESCRIPTION OF THE DRAWINGS

In the following description, the present invention will be explained in more detail by means of exemplary embodiments and with reference to the drawings, wherein FIG. 1—shows a schematic diagram of an extraoral X-ray system according to one embodiment.

DETAILED DESCRIPTION OF THE INVENTION

Figure 1:
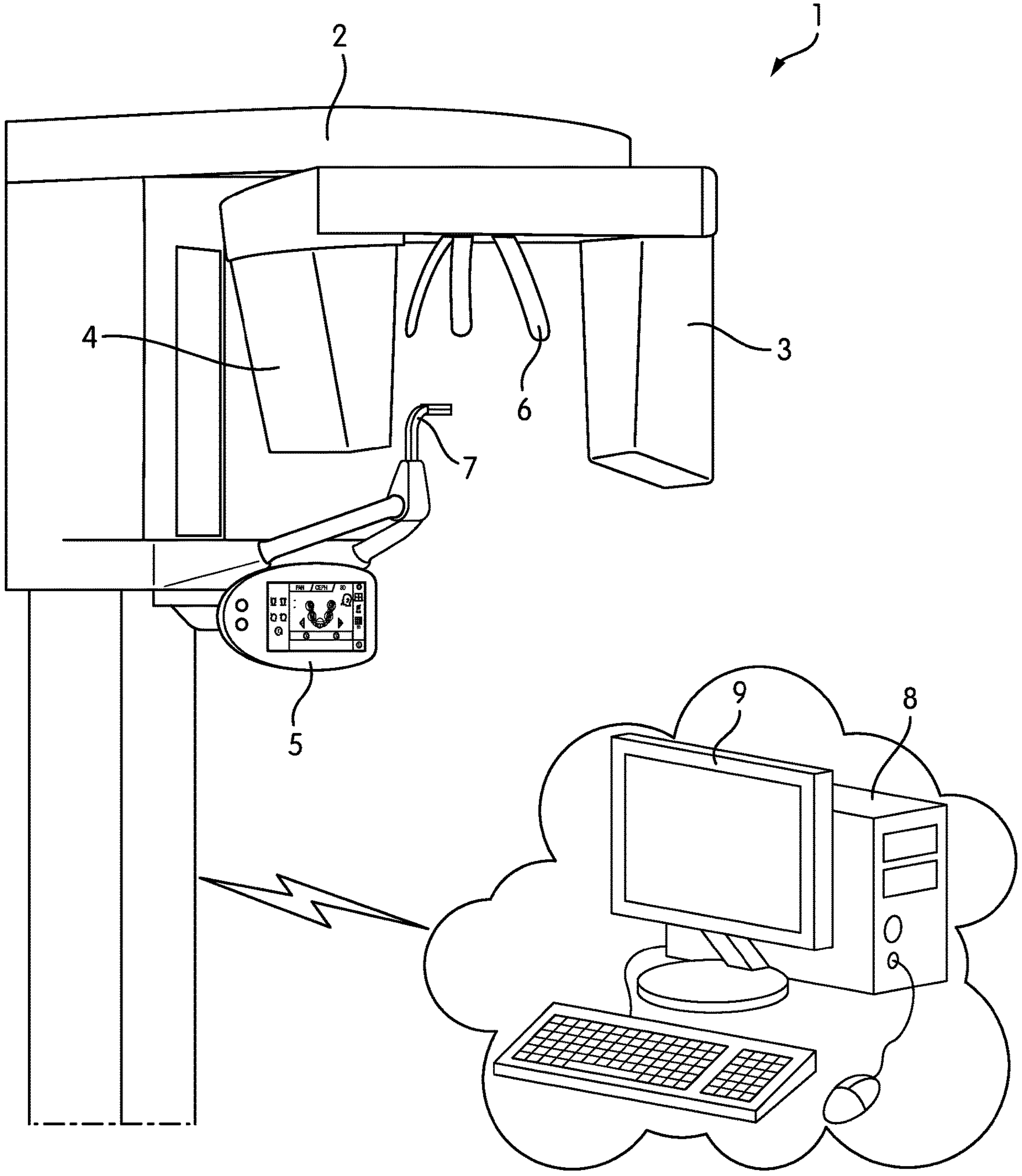

The reference numbers shown in the drawings designate the elements listed below, which are referred to in the following description of exemplary embodiments.

1. Extraoral X-ray system
2. X-ray device
3. X-ray source
4. X-ray detector
5. Control unit/panel
6. Head fixation
7. Bite block
8. Computer
9. Display
10. Patient
11*a*. Jaw arch form
11*b*. Tooth
12. Imaging trajectory (patient-specific)
12*a*. X-ray source trajectory
12*b*. X-ray detector trajectory
13. Imaging trajectory (X-ray device default)
13*a*. X-ray source trajectory
13*b*. X-ray detector trajectory
14. Focal curve (patient-specific)
15. Focal curve (x-ray device default)

The method according to the invention is used to produce a panoramic image.

Figure 2:
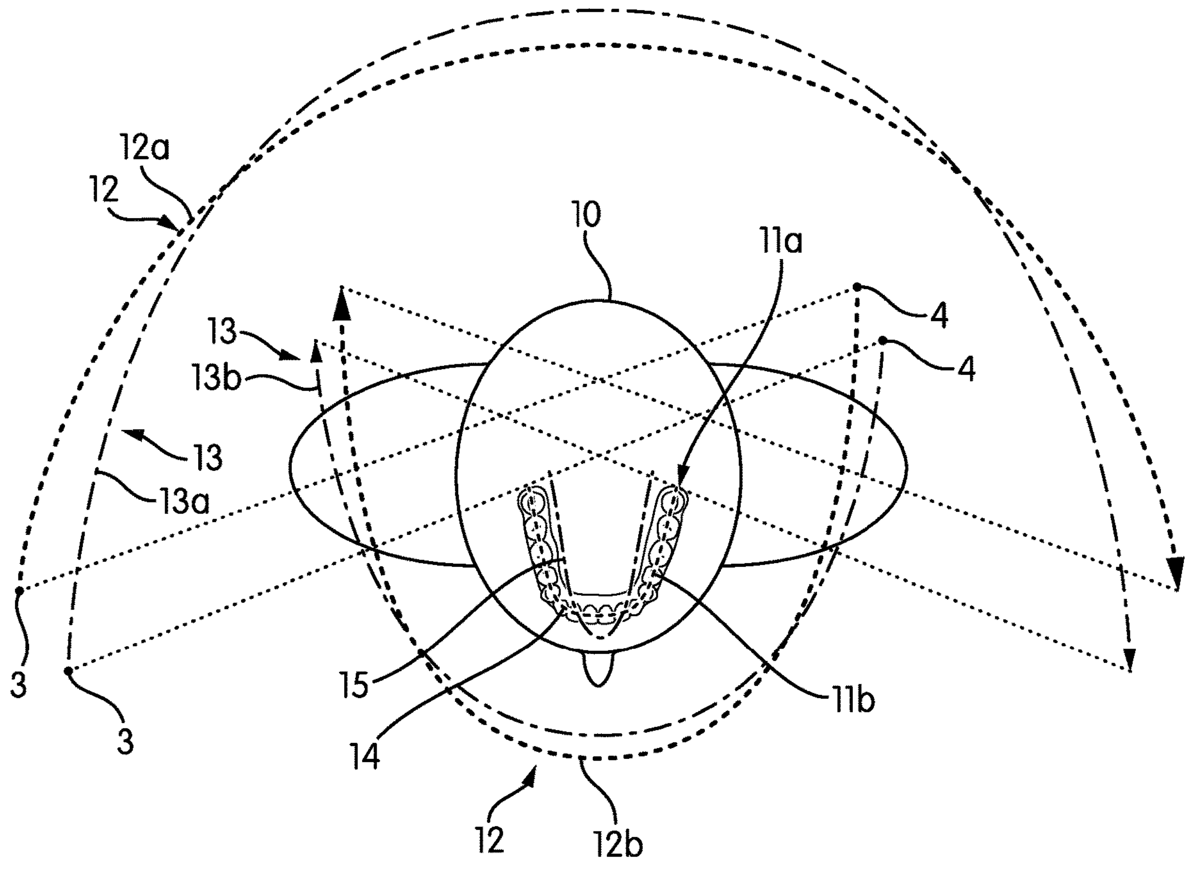
FIG. 2—shows a schematic representation of an extraoral panoramic imaging according to the determined patient-specific imaging trajectory and patient-specific focal curve.

In a first step S1, based on one or more previous panoramic images or one or more previous 3D images or one or more previous optical 3D scans of a patient, the jaw arch form (11*a*) (see FIG. 2) is determined as a model-based prior knowledge about the anatomy of the patient (10). This prior knowledge can optionally be stored and retrieved for later use. In a further step S2, the model-based prior knowledge is used to determine a patient-specific imaging trajectory (12) (see FIG. 2) for the panoramic image of the patient (10) to be produced so that the jaw arch shape (11*a*), especially the position of the teeth (11*b*) can be optimally exposed and recorded. The patient-specific imaging trajectory (12) consists of the patient-specific X-ray source trajectory (12*a*) and the patient-specific X-ray detector trajectory (12*b*). As FIG. 2 shows, in a further step S3, the imaging is performed based on the determined patient-specific imaging trajectory (12). The patient-specific imaging trajectory (12) is adjusted so that the dental structures along the jaw arch form (11*a*) of the maxilla and mandible can be irradiated by the X-ray source and fully detected by the X-ray detector. The X-ray device's default imaging trajectory (13) might not completely or correctly expose, and record said dental structures e.g., especially the molars or the anterior teeth. For comparison, the X-ray device default imaging trajectory (13) is also shown in FIG. 2. The X-ray device default imaging trajectory (13) consists of the X-ray source default trajectory (13*a*) and the X-ray detector default trajectory (13*b*). In a further step S4, the reconstruction parameters are adjusted according to the determined patient-specific imaging trajectory (12). The reconstruction parameters are adapted to the jaw arch form of the upper and lower jaws in a patient-specific manner. In a further step S5, the model-based prior knowledge is used to determine the patient-specific focal curve (14) (see FIG. 2) of the panoramic image of the patient (10), to be produced so that the mandibular arch form (11*a*) and especially the position of the teeth (11*b*) can be optimally reconstructed. Alternatively, separate patient-specific focal curves (14) can be used for the reconstruction of the maxilla and mandible based on the said prior knowledge. For comparison, the X-ray device default focal curve (15) is also shown in FIG. 2. In a further step S6, a panoramic image is reconstructed using the exposure data, the adjusted reconstruction parameters including the determined patient-specific focal curve (14) and a layer to be imaged which overlaps with the determined jaw arch form (11*a*). The patient-specific focal curve (14) lies within said layer to be imaged (sharp layer). The overlap of the jaw arch form (11*a*) and the sharp layer is preferably maximum. In a further step S7, the reconstructed panoramic image is displayed. When the reconstructed panoramic image is displayed, the dental structures in the sharp layer are displayed. The sharp layer contains the dental structures of the jaw arch form (11*a*) to be mapped in the panoramic image. For the reconstruction of the panoramic image, the acquired 2D x-ray projection images resulting during the acquisition along the patient-specific imaging trajectory are computed based on the position of the layer to be imaged, for example, by means of an shift & add procedure. Other known methods can also be used.

The method according to the invention is a computer-implemented method and can be executed on a computer-assisted extraoral X-ray system (1). FIG. 1 shows an example of the extraoral X-ray system (1). The method according to the invention is implemented by a computer program comprising computer-readable code. The computer program may be provided on a data storage device. As shown in FIG. 1, the computerized extraoral X-ray system (1) comprises an X-ray device (2) for performing patient imaging, whereby individual 2D X-ray images are generated. The X-ray unit (2) has an X-ray source (3) and X-ray detector (4), which are rotated around the patient's head during the exposure. The X-ray device (2) has a rotation mechanism whereby the X-ray source (3) and the X-ray detector (4) can be rotated around the patient's head according to the determined patient-specific imaging trajectory curve (12) or, alternatively, according to the X-ray device default imaging trajectory (13). The rotation mechanism allows the patient-specific imaging trajectory (12) to be traversed. The X-ray device (2) can also be controlled so that the default imaging trajectory (13) for the X-ray device (2) is traversed. The trajectories (12;13) can describe a circular path. Alternatively, they can assume a more complex curve shape deviating from this by the use of a plurality of actuators. Before the exposure, the patient's head is positioned in the X-ray device (2) with the bite block (7) and the head fixation (6). As shown in FIG. 1, the computerized extraoral X-ray system (1) has an operating unit (5), preferably a separate computer (8) or computing unit that can be connected to the X-ray device (2), and preferably a separate display (9), inter alia to visualize data sets resulting from the method. The computer (8) can be connected to the X-ray device (2) via a local network (not shown) or alternatively via the Internet. The computer (8) may be part of a cloud. Alternatively, the computer (8) may be integrated into the X-ray device (2). The computations can take place in the computer (8) or in the cloud. For this purpose, the raw imaging data can be transmitted in compressed form. The computer (8) executes the computer program and provides the data sets, including for the visualization on the display (9). The display (9) can be spatially separated from the X-ray device (2). Preferably, the computer (8) can also control the X-ray device (2). Alternatively, separate computers (8) may be used for control and image processing. According to the present invention, the data sets generated by the above embodiment may be presented to a physician for visualization, in particular for diagnostic purposes, preferably by means of a display (9) or a printout.

In a preferred embodiment, the jaw arch form (11*a*) is determined using one or more neural networks. The neural networks are trained by data pairs each comprising e.g., a 3D volume and the jaw arch form (11*a*) marked therein, or e.g., an optical 3D scan and the jaw arch form (11*a*) marked therein. The jaw arch form (11*b*) may have been marked manually or automatically by image processing considering anatomical dental features. The neural networks may be provided integrated with the extraoral X-ray system (1). Alternatively, the neural networks can be provided separately. The extraoral X-ray system (1) may be connected to the neural networks locally or via a network. The neural networks can be implemented by hardware and/or software.

The invention claimed is:

1. A method of producing a panoramic image comprising:

determining a jaw arch form as a model-based prior knowledge about an anatomy of a patient based on one or more previous panoramic images or 3D images or optical 3D scans of the patient, wherein the jaw arch form is determined using a neural network, wherein the neural network is trained by data pairs each comprising a 3D volume and the jaw arch form marked therein, or comprising an optical 3D scan and the jaw arch form marked therein;

determining a patient-specific x-ray device imaging trajectory for the panoramic image of the patient to be produced by using the model-based prior knowledge so that the determined jaw arch from, and in particular a position of teeth thereof is exposed and imaged;

performing an imaging on the basis of the determined patient-specific x-ray device imaging trajectory to acquire imaging data;

adjusting reconstruction parameters of the x-ray device according to the determined patient-specific x-ray device imaging trajectory;

determining a patient-specific focal curve for the panoramic image of the patient to be produced by using the model-based prior knowledge so that the determined jaw arch form, and in particular the position of the teeth therein is reconstructed;

reconstructing the panoramic image using the acquired imaging data, the adjusted reconstruction parameters including the determined patient-specific focal curve, and a layer to be imaged which overlaps with the determined jaw arch form, wherein the patient-specific focal curve lies within said layer to be imaged; and displaying the reconstructed panoramic image.

2. The method according to claim 1, wherein the jaw arch form is marked manually or automatically by image processing while taking into account anatomical features of the patient.

3. The method according to claim 1, wherein during the reconstruction, the overlap of the jaw arch form and the layer to be imaged is maximal.

4. A non-transitory computer-readable storage medium, including instructions for producing a panoramic image that when executed by a computer, cause the computer to:

determine a jaw arch form as a model-based prior knowledge about an anatomy of a patient based on one or more previous panoramic images or 3D images or optical 3D scans of the patient, wherein the jaw arch form is determined using a neural network, wherein the neural network is trained by data pairs each comprising a 3D volume and the jaw arch form marked therein, or comprising an optical 3D scan and the jaw arch form marked therein;

determine a patient-specific x-ray device imaging trajectory for the panoramic image of the patient to be produced by using the model-based prior knowledge so that the determined jaw arch from, and in particular a position of teeth thereof is exposed and imaged;

perform an imaging on the basis of the determined patient-specific x-ray device imaging trajectory to acquire imaging data;

adjust reconstruction parameters of the x-ray device according to the determined patient-specific x-ray device imaging trajectory;

determine a patient-specific focal curve for the panoramic image of the patient to be produced by using the model-based prior knowledge so that the determined jaw arch form, and in particular the position of the teeth therein is reconstructed;

reconstruct the panoramic image using the acquired imaging data, the adjusted reconstruction parameters including the determined patient-specific focal curve, and a layer to be imaged which overlaps with the determined jaw arch form, wherein the patient-specific focal curve lies within said layer to be imaged; and display the reconstructed panoramic image.

5. A computerized extraoral x-ray system comprising an x-ray device, a processor; and a memory storing instructions for producing a panoramic image that, when executed by the processor, configure the system to:

determine a jaw arch form as a model-based prior knowledge about an anatomy of a patient based on one or more previous panoramic images or 3D images or optical 3D scans of the patient, wherein the jaw arch form is determined using a neural network, wherein the neural network is trained by data pairs each comprising a 3D volume and the jaw arch form marked therein, or comprising an optical 3D scan and the jaw arch form marked therein;

determine a patient-specific x-ray device imaging trajectory for the panoramic image of the patient to be produced by using the model-based prior knowledge so that the determined jaw arch from, and in particular a position of teeth thereof is exposed and imaged;

perform an imaging on the basis of the determined patient-specific x-ray device imaging trajectory to acquire imaging data;

adjust reconstruction parameters of the x-ray device according to the determined patient-specific x-ray device imaging trajectory;

determine a patient-specific focal curve for the panoramic image of the patient to be produced by using the model-based prior knowledge so that the determined jaw arch form, and in particular the position of the teeth therein is reconstructed;

reconstruct the panoramic image using the acquired imaging data, the adjusted reconstruction parameters including the determined patient-specific focal curve, and a layer to be imaged which overlaps with the determined jaw arch form, wherein the patient-specific focal curve lies within said layer to be imaged; and display the reconstructed panoramic image.

* * * * *